US 6,887,261 B1

(12) United States Patent
Peyman (10) Patent No.: US 6,887,261 B1
(45) Date of Patent: May 3, 2005

(54) SYSTEM AND METHOD FOR THERMALLY AND CHEMICALLY TREATING CELLS AT SITES OF INTEREST IN THE BODY TO IMPEDE CELL PROLIFERATION

(76) Inventor: Gholam A. Peyman, 8654 Pontchartrain Blvd., Unit #1, New Orleans, LA (US) 70124

( * ) Notice: Subject to any disclaimer, the term of this patent is extended or adjusted under 35 U.S.C. 154(b) by 208 days.

(21) Appl. No.: 09/840,975

(22) Filed: Apr. 25, 2001

(51) Int. Cl.$^7$ .............................................. A61N 5/067
(52) U.S. Cl. ......................................... 607/89; 607/92
(58) Field of Search ...................... 607/88–92; 606/4–6, 606/15, 41

(56) References Cited

U.S. PATENT DOCUMENTS

| | | | |
|---|---|---|---|
| 4,846,172 A | * 7/1989 | Berlin | 606/4 |
| 4,911,163 A | 3/1990 | Fina | 606/127 |
| 5,290,295 A | 3/1994 | Querals et al. | 606/108 |
| 5,439,446 A | 8/1995 | Barry | 604/96 |
| 5,514,092 A | 5/1996 | Forman et al. | 604/101 |
| 5,549,596 A | * 8/1996 | Latina | 606/4 |
| 5,785,675 A | 7/1998 | Drasler et al. | 604/22 |
| 5,851,210 A | 12/1998 | Torossian | 606/108 |
| 5,885,279 A | * 3/1999 | Bretton | 606/41 |
| 5,968,033 A | * 10/1999 | Fuller et al. | 606/9 |
| 6,059,809 A | 5/2000 | Amor et al. | 606/108 |
| 6,066,138 A | 5/2000 | Sheffer et al. | 606/49 |
| 6,491,715 B1 | * 12/2002 | Abels et al. | 607/89 |

OTHER PUBLICATIONS

Reichel, Elias et al., ICG Dye–Enhanced Diode Laser Photocoagulation of Poorly Defined Subfoveal Choroidal Neovascularization, Ophthalmic Surgery, Mar. 1994, pp. 195–201.*

* cited by examiner

Primary Examiner—Roy D. Gibson
(74) Attorney, Agent, or Firm—Roylance, Abrams, Berdo & Goodman, L.L.P.

(57) ABSTRACT

A system and method for treating cells of a site in the body, such as at a lens capsule or choroid of an eye. The system and method employs an energy emitting device, and a positioning device, adapted to position the energy emitting device at a position in relation to the cells at the site in the body, such as the cells of the choroid or the lens capsule, so that energy emitted from the energy emitting device heats the cells to a temperature which is above body temperature and below a temperature at which protein denaturation occurs in the cells, to kill the cells or impede multiplication of the cells. The energy emitting device can also include a container containing a heated fluid that can include indocyanine green, which heats the cells to the desired temperature. Alternatively, the energy emitting device can include a laser diode, or a probe that emits radiation, such as infrared or ultraviolet radiation, laser light, microwave energy or ultrasonic energy. The system and method can further employ a material delivery device that can be unitary with or separate from the energy emitting device, an can provide a material, such as indocyanine green, to the cells at the site of interest. A light emitting device can be controlled to direct light onto the site of interest to activate the material present at the cells to alter a physical characteristic of the cells.

50 Claims, 8 Drawing Sheets

SYSTEM AND METHOD FOR THERMALLY AND CHEMICALLY TREATING CELLS AT SITES OF INTEREST IN THE BODY TO IMPEDE CELL PROLIFERATION

RELATED APPLICATIONS

This application is related to application Ser. No. 09/494,248, filed Jan. 31, 2000, the entire of which is herein incorporated by reference.

BACKGROUND OF THE INVENTION

1. Field of the Invention

The present invention relates to a system and method for treating cells at a site in the body, such as at a lens capsule or choroid of an eye, thermally and, if desired, chemically. More particularly, the present invention relates to a system and method for treating cells at a site in the body, such as at a lens capsule of an eye, by applying energy to the cells to heat the cells to a temperature which will kill the cells or impede cell multiplication without causing protein denaturation to occur in the cells, and, if desired, by further exposing the cells to a material which alters a physical characteristic of the cells to kill the cells or further impede cell multiplication.

2. Description of the Related Art

Several techniques currently exist for treating cells at a selected site in the body with heat or chemicals to kill or impede multiplication of those cells to prevent undesired cell proliferation. For example, numerous types of chemotherapy drugs exists which, when injected into a tumor or delivered systemically to a patient, attack and kill cancerous cells to prevent them from further multiplying.

Radiation techniques can also be used to kill cancerous or other undesired cells. That is, when cells are heated to a temperature of about 5° C. or more above the normal body temperature of 37° C., cell death begins to occur. Applying radiation to a localized site in the body, such as a tumor or other area containing undesired cells, can heat the cells at the site to temperatures in excess of 60° C. Such high temperatures cause a phenomenon known as protein denaturation to occur in the cells, which results in immediate cell death. Accordingly, radiation therapy has been suitable in successfully treating certain types of cancers and other diseases involving uncontrolled cell growth.

Other types of heating techniques, such as the use of probes or catheters to provide localized heat to a site of interest also exist. Like radiation therapy, these techniques also heat the cells to a high enough temperature to cause protein denaturation in the cells to thus kill the cells quickly.

In addition, it is also known to use photosensitive chemicals to kill cells at certain sites of interest in the body. For example, a photosensitive chemical can be injected directly into a site of interest to expose cells at that site to the chemical. A light emitting source which emits light at a wavelength that will activate the photosensitive chemical is then focused on the site of interest. Accordingly, the light activates the photosensitive chemical that has been absorbed by or is otherwise present in the cells of interest. The activated chemical kills the cells, which thus prevents undesired cell proliferation.

Although the techniques mentioned above can be suitable for preventing certain types of cell proliferation and certain sites in the body, several drawbacks with these techniques exist. For example, often the use of chemotherapy drugs alone to treat a tumor or cancerous site is insufficient to kill the undesired cells. Moreover, the chemotherapy drugs also kill many normal healthy cells along with the cancerous cells, which can adversely affect the patient's health.

The use of radiation in conjunction with chemotherapy can have a more detrimental effect on the cancerous cells. However, as with chemotherapy, radiation often kills normal healthy cells, such as those in front of or behind the site of interest, along with the cancerous cells. Moreover, the intense heating of the cells can cause the cells to coagulate and thus block the capillaries at the site of interest. The blocked capillaries therefore prevent chemotherapy drugs from reaching the site of interest.

In addition, is it not known to use the above techniques to prevent unwanted cell proliferation at certain locations in the eye, such as at the retina or at the lens capsule. For example, because the retina is very sensitive, known radiation techniques can be too severe to treat cancerous cells on, in or under the retina.

Also, after cataract surgery, a phenomenon known as capsular opacification and, in particular, posterior capsular opacification can occur in which the epithelial cells on the lens capsule of the eye experience proliferated growth. This growth can result in the cells covering all or a substantial portion of the front and rear surfaces of the lens capsule, which can cause the lens capsule to become cloudy and thus adversely affect the patient's vision. These cells can be removed by known techniques, such as by scraping away the epithelial cells. However, it is often difficult to remove all of the unwanted cells. Hence, after time, the unwanted cells typically will grow back, thus requiring further surgery.

Accordingly, a need exists for a system and method for preventing unwanted cell proliferation at sites in the body, especially at sites in the eye such as the retina and lens capsule, which does not suffer from the drawbacks associated with the known techniques discussed above.

SUMMARY OF THE INVENTION

An object of the present invention is to provide a system and method for preventing the proliferation of unwanted cells at various sites in the body, especially at sites in the eye such as the choroid, retina and lens capsule.

Another object of the invention is to provide a system and method for thermally and chemically treating cells at sites in the body to kill the cells or impede cell multiplication without causing protein denaturation to occur in the cells.

A further object of the present invention is to provide a system and method which uses an energy emitting device to heat cells at a site of interest in the body to a temperature which kills the cells without causing protein denaturation in the cells, and which also chemically treats the cells, if desired, to change a physical characteristic of the cells to thus cause cell death or impede cell multiplication.

These and other objects of the invention are substantially achieved by providing a system and method for treating cells of a site in the body, such as at a lens capsule or choroid of an eye. The system and method employs an energy emitting device, and a positioning device, adapted to position the energy emitting device at a position in relation to the cells at the site in the body, such as the cells of the lens capsule or choroid, such that energy emitted from the energy emitting device heats the cells to a temperature which is above body temperature and below a temperature at which protein denaturation occurs in the cells, to kill the cells or impede multiplication of the cells. The energy emitting device can include a container containing a heated fluid which heats the cells to the desired temperature, a portion of the heated fluid being indocyanine green.

The system and method can further employ a material delivery device that can be unitary with or separate from the energy emitting device, an can provide a material, such as indocyanine green, to the cells at the site of interest. A light emitting device can be controlled to direct light onto the site of interest to activate the indocyanine green present at the cells to alter a physical characteristic of the cells.

BRIEF DESCRIPTION OF THE DRAWINGS

These and other objects, advantages and novel features of the invention will be more readily appreciated from the following detail description when read in conjunction with the accompanying drawings, in which.

DETAILED DESCRIPTION OF THE PREFERRED EMBODIMENTS

Figure 1:
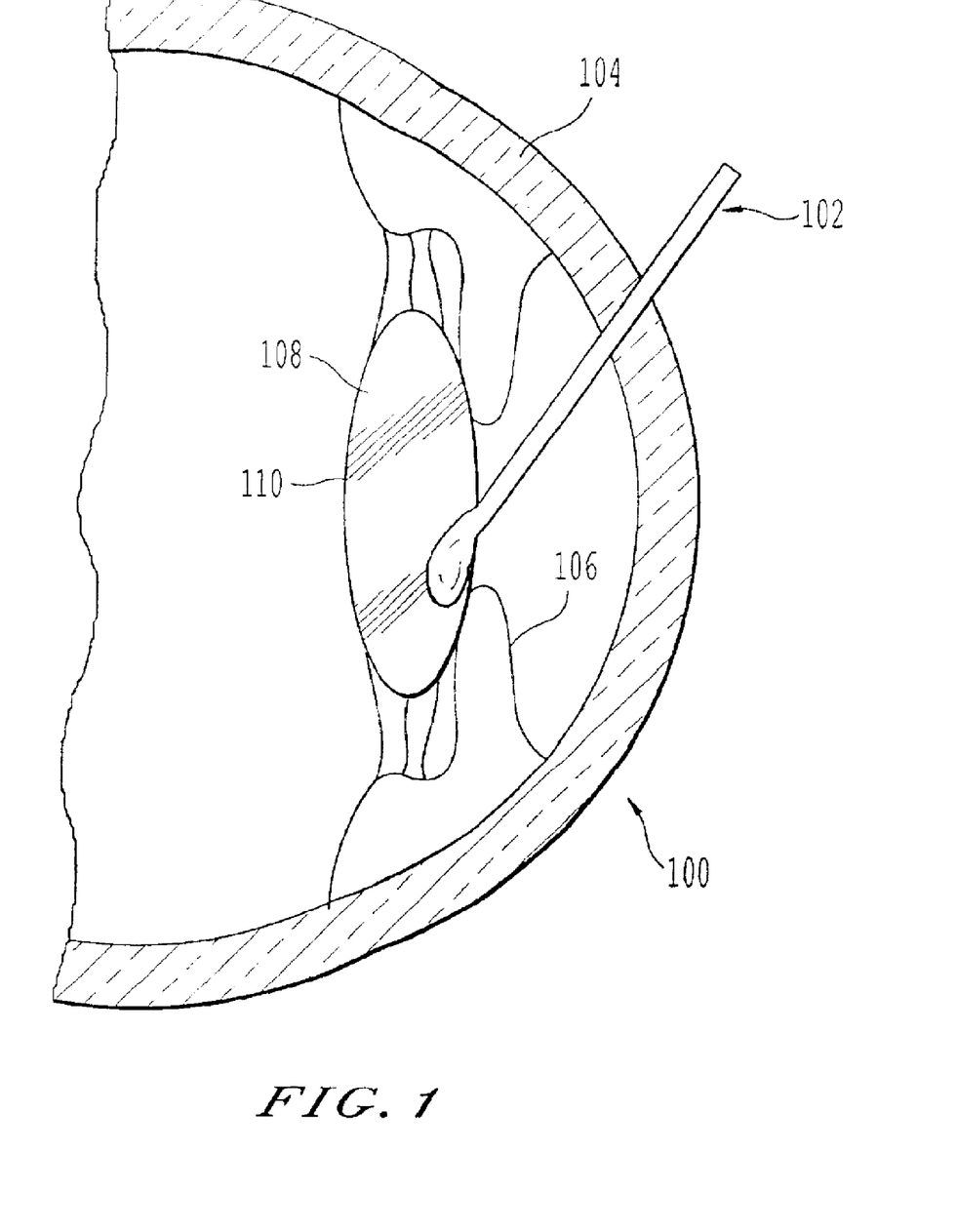
FIG. 1 is a cross-sectional view of an eye into which a device for treating cells according to an embodiment of the present invention is being inserted.

FIG. 1 is a cross-sectional view of an eye 100 into which is being inserted a device 102 for treating cells according to an embodiment of the present invention. As shown, the eye 100 includes a cornea 104, an iris 106, and a lens 108 having a lens capsule 110. In this example, the device 102 is being used to treat epithelial cells of the lens 108 that has undergone or is undergoing a cataract procedure.

As discussed in the Background section above, it is known in the art that after cataract surgery has been performed on a lens of an eye, the epithelial cells of the lens can proliferate on the front and rear surfaces of the lens capsule. This cell proliferation is known as capsular opacification, which causes the lens capsule to become cloudy and thus adversely affect vision. As will now be described, the device 102 can be used to treat the epithelial cells of the lens to kill or impede cell growth, and thus prevent or minimize capsular opacification. Specifically, the device 102 can be used to apply a hyperthermia treatment (heating) to the cells to kill the cells or impede cell growth.

As mentioned in the Background section above, when cells are heated to a temperature of about 5° C. or more above the normal body temperature of 37° C., cell death begins to occur. Specifically, heating cells to a temperature between about 42° C. and about 50° C. causes cell death. Heating cells to higher temperatures, such as about 60° C. and above, causes protein denaturation to occur in the cells, which results in immediate cell death. The protein denaturation phenomenon also causes coagulation of the cells in the heated area.

It is also known that cells can tolerate certain drugs or chemicals at normal body temperature or slightly above normal body temperature. However, as the temperature of the cells is increased to, for example, about 42° C. or above, drugs that are normally tolerated by the cells at normal temperature can have a deleterious effect on the cells at these higher temperatures. The device 102 uses the effect of temperature and, if desired, chemicals to treat the cells of the lens capsule 110 to prevent or impede cell proliferation.

Figure 2:
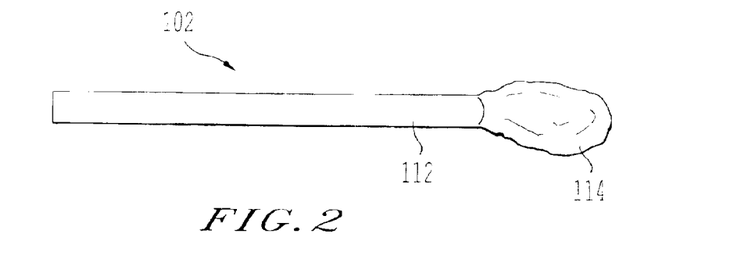
FIG. 2 illustrates a device according to the present invention as shown in FIG. 1.
Figure 3:
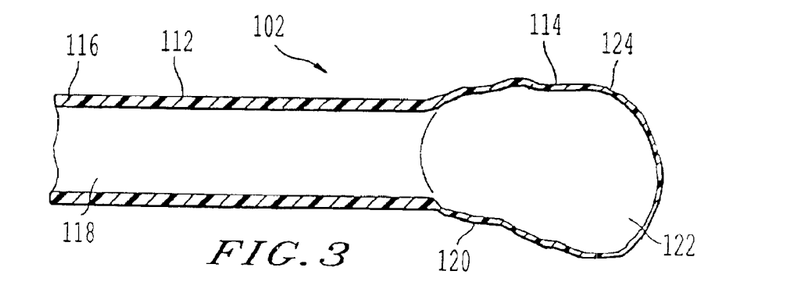
FIG. 3 is a cross-sectional view of the device show in FIG. 2.

As shown in FIGS. 2 and 3, device 102 includes a shaft portion 112 and an expandable portion 114. The device 102 can be made of a synthetic material such as silicone, plastic or any other suitable material. The shaft portion 112 includes a wall portion 116 and a chamber 118. The wall portion 116 can include an insulating material, or can have a thickness sufficient to insulate the chamber 118 from the environment outside the shaft portion 112. Also, the wall portion 116 can include a chamber that is filled, for example, with air which acts as a insulator.

As further illustrated, the shaft portion 112 in this example is integral with the expandable portion 114. However, the device 102 can be configured so that the shaft portion 112 is attachable to the expandable portion 114. Expandable portion 114 has a wall portion 120 that can be made of the same material as shaft portion 112, or any other suitable expandable material. The wall portion 120 defines a chamber 122 that is in communication with chamber 118 of shaft portion 112. The wall portion 120 can be porous to allow liquid to pass therethrough, or can have one or more openings 124 therein, if desired, to allow fluid collected in chamber 122 to pass therethrough. However, the wall portion 120 can also be impermeable to fluid, if desired.

In the example shown in FIG. 1, the device 102 is used to treat the cells and, in particular, the epithelial cells on the anterior and posterior surfaces of the lens capsule 110 on which cataract surgery is being or has been performed. As can be appreciated by one skilled in the art, to perform cataract surgery, a small incision is made in the cornea 104 of the eye 100, and a small incision is made in the lens capsule 110. The cortex and nucleus of the lens 108 is removed through the small opening in the lens capsule 110.

The expandable portion 114 of the device 102, along with some of the shaft portion 112, if necessary, is inserted into the small incision in the lens capsule 110. A heated fluid such as water or saline solution or any other suitable solution is provided into the chamber 118 of the shaft portion 112, and flows into the chamber 122 of the expandable portion 114. The liquid also can be viscous or semiviscous, if desired.

In one example, the fluid has been heated to a temperature of about 40° C. to about 100° C. and, preferably, between about 42° C. to about 60° C. A device (not shown) controls the temperature of the fluid to maintain the temperature within the desired range. The device also controls the pressure at which the fluid is provided into the chamber 122 to expand the expandable portion 114 in a balloon-like manner by a desired amount. Furthermore, a timing device can be used to monitor the time during which the expandable portion 114 should remain in contact with the cells, which can be within a range of about 1 minute or about 10 minutes, or any suitable period of time to achieve the desired results.

Accordingly, the temperature of the liquid in the chamber 122 of the expandable portion 114 heats the cells surrounding and in proximity to the expanded expandable portion 122 to a desired temperature within a range of about 45° C. to about 50° C. Although the cells heated to this temperature will die, the cells will not experience protein denaturation. Therefore, these cells will not coagulate and will not cloud the lens capsule 110. The time during which the expandable portion 114 having the heated solution therein is maintained in contact with the cells also is closely monitored to assure that underheating or overheating does not occur.

The expandable portion 114 can be placed inside the anterior of the lens capsule 110, the posterior of the lens capsule 110, or at the outside anterior and posterior surfaces of the lens capsule 110 instead of inside the lens capsule to kill the epithelia cells. It can be also noted that the expandable portion 114 of the device 102 can be inserted into the lens capsule 110, or can be placed on the outside surfaces of the lens capsule 110, before the cortex, the nucleus, or both, have been removed.

It is further noted that a drug or material can be included in the heated fluid 114 when the heated fluid is being provided into chamber 116 and thus into chamber 122, or can be added to the fluid in the chamber 122 via chamber 116 at an appropriate time. The drug or material can be of the type that can be tolerated by cells under normal temperature, but which can enhance cell death at the elevated temperature. These drugs or chemicals can be antiproliferative or anticancer drugs, antibiotics which act on cell membranes or internal structures of the cells, agents which act as surfactants, or agents which contain alcohol at various concentrations. Also, the chemicals can be photosensitizers for reasons described in more detail below. These chemicals and drugs can pass through the porous membrane of the wall 120 of expandable portion 114, or through the openings in expandable portion 114, to come in contact with and be absorbed by the cells. Alternatively, if a device 102 having a non-porous expandable portion 114 or an expandable portion 114 having no openings therein is used to heat the cells, that device can be removed and replaced with another device 102 having a porous expandable portion 114 or an expandable portion 114 having openings therein, so that the drugs or chemicals can be delivered to the cells through this second device.

After the expandable portion 114 has been kept in contact with the cells for the appropriate length of time, the expandable portion 114 can be deflated and removed from the lens capsule 110. Alternatively, instead of removing the expandable portion 114 right away, the expandable portion 114 can be allowed to remain deflated in the lens capsule 110 for a desired period of time, and then reexpanded to repeat the heating process and/or the drug or chemical delivery process described above. Once the treatments have been completed, the expandable portion 114 can be deflated and removed from the lens capsule 110. An artificial lens can then be implanted inside the lens capsule 110.

Figure 4:
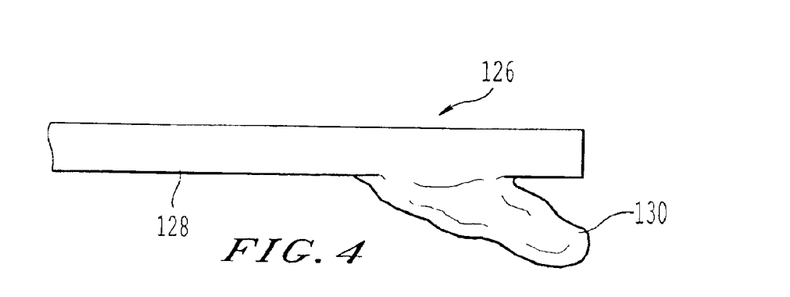
FIG. 4 is an example of a modification to the device shown in FIG. 2.
Figure 5:
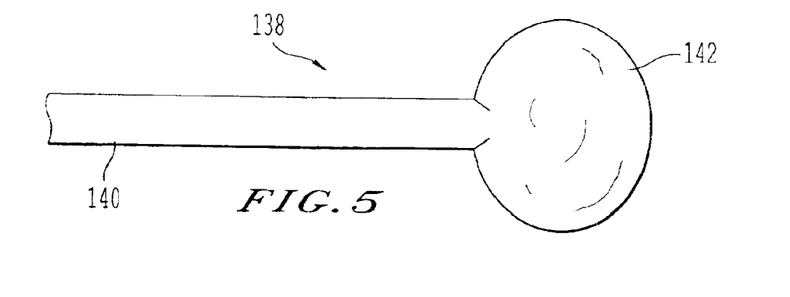
FIG. 5 is an example of another modification to the device shown in FIG. 2.
Figure 6:
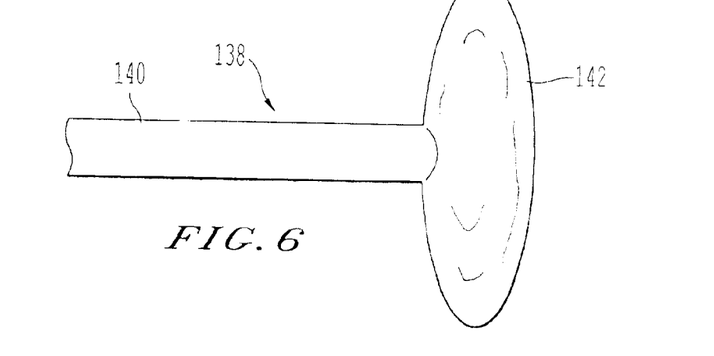
FIG. 6 is an example of a further modification to the device shown in FIG. 2.
Figure 7:
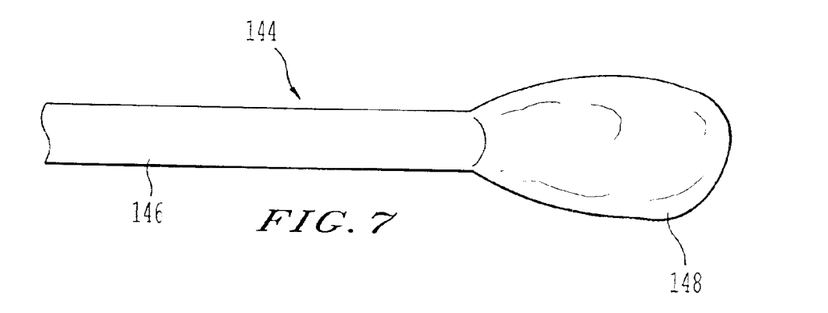
FIG. 7 is an example of still a further modification to the device shown in FIG. 2.
Figure 8:
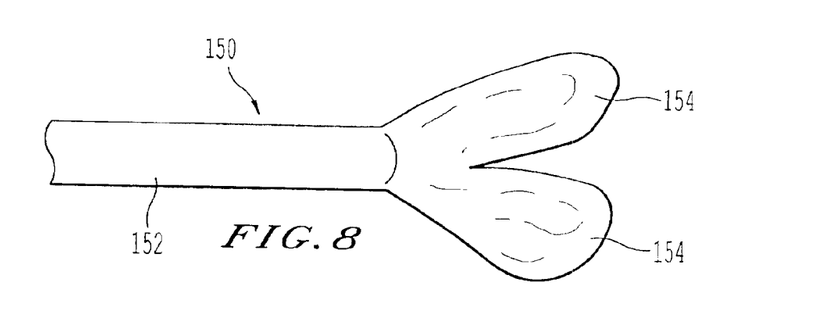
FIG. 8 is an example of another modification to the device shown in FIG. 2.

It is noted that the device 102 need not be configured as shown in FIG. 2. Rather, as shown in FIG. 4, the device can be configured as a device 126 having a shaft portion 128 and an expandable portion 130 at a position along the shaft portion 128 as illustrated. The device can alternatively be configured as device 132 as shown in FIG. 5, having a shaft portion 134 and round or substantially round expandable portion 136. The device can alternatively be configured as device 138 as shown in FIG. 6, having a shaft portion 140 and a disc-shaped expandable portion 142. Also, the device can be configured as device 144 as shown in FIG. 7, having a shaft portion 146 and extended expandable portion 148. Furthermore, the device can be configured as device 150 as shown in FIG. 8, having a shaft portion 152 and two or more expandable portions 154.

Figure 9:
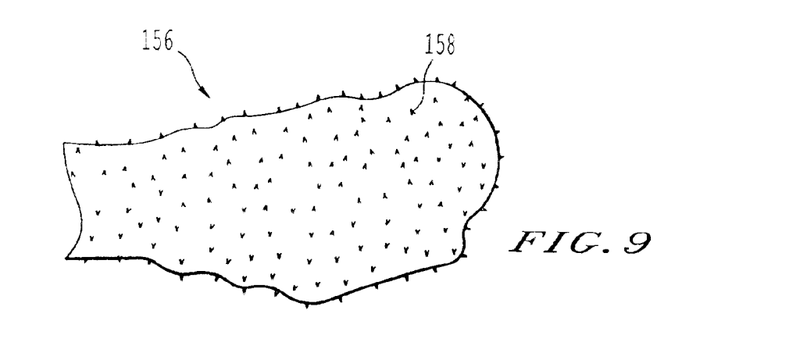
FIG. 9 is a detailed example of a rough surface that can be present on the expandable container of the devices shown, for example, in FIGS. 2 and 4–8.

It is further noted that the devices shown in FIGS. 4 through 8 can be made of the same or substantially the same materials as device 102 shown in FIG. 2, and can function in substantially the same manner as device 102. The expandable portions of all the devices shown in FIGS. 2 and 4–8 can be porous or include openings as described above, or be non-porous and include no openings. Furthermore, the expandable portions of all the devices shown in FIGS. 2 and 4 through 8 can be configured as expandable portion 156 shown in FIG. 9, which includes ridges or abrasive portions 158 on its exterior. These ridges or abrasive portions can be used to remove dead cells from the site of interest if the device is moved so that its expandable portion rubs against the site of interest.

Figure 10:
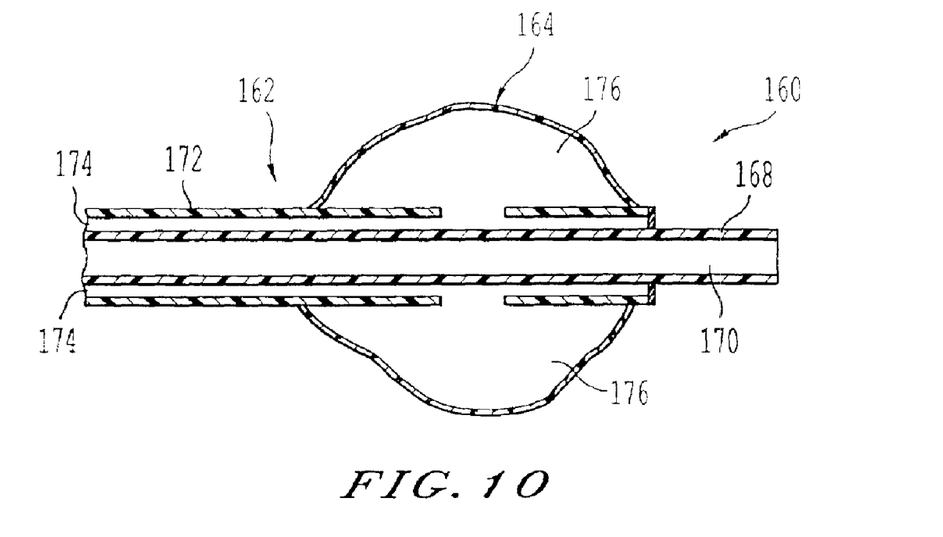
FIG. 10 is an cross-sectional view of another modification to the device shown in FIG. 2.

As shown in FIG. 10, the device can be configured as a device 160 having a shaft portion 162 and an expandable portion 164. The expandable portion 164 in device 160 is similar to the expandable portions of all the device shown in FIGS. 2 and 4 through 8 as discussed above. However, as illustrated, the expandable portion 164 is at a distance from the distal end 166 of the shaft portion 162.

Furthermore, the shaft portion 162 includes an inner shaft 168 defining a chamber 170, and an outer shaft 172 which defines a chamber 174 between its inner wall and the outer wall of shaft 168. The shaft portion 162 and expandable portion 164 can be made of the same or substantially the same materials as the shaft portion and expandable portions of the devices discussed above. However, in this example, the chamber of shaft portion 168 does not communicate with the interior chamber of expandable portion 164. Rather, the chamber 170 defined by shaft 168 can pass through the shaft portion 162 to therefore allow fluid to pass through shaft portion 162 to the site of interest, or to allow fluid to be aspirated from the site of interest through chamber 170. Alternatively, the distal end of the shaft portion 162 can be closed. The chamber 174, on the other hand, can be used to introduce fluid into the chamber 176 of the expandable portion 164. This fluid can be heated fluid as discussed above with regard to device 102 to heat the cells at the site of interest to kill the cells or impede cell multiplication without causing protein denaturation. The drugs or chemicals described above can also be added to the fluid for the purposes described above.

Figure 11:
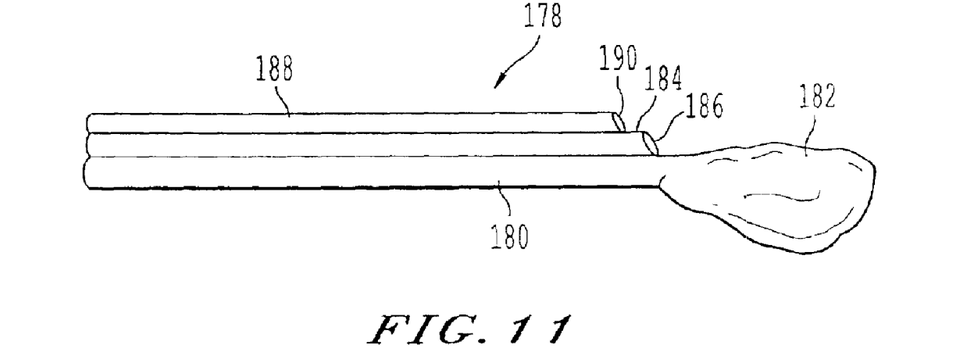
FIG. 11 is an example of still a further modification to the device shown in FIG. 2, which includes additional tubes for irrigating and aspirating the site of interest.

As shown in FIG. 11, the device can be configured as device 178 having a shaft portion 180 and an expandable portion 182 which can be similar to the shaft portion 112 and expandable portion 114 of device 102. However, device 178 can also include a first tube 182 defining a chamber 186 therethrough, and a second tube 188 defining a chamber 190 therethrough. As can be appreciated by one skilled in the art, tubes 184 and 188 can be used to irrigate and aspirate the site of interest that is being treated by the expandable portion 182. That is, a fluid, such as water or a saline solution, can be ejected from chamber 186 of tube 184 to the site of interest, and then aspirated through chamber 190 of tube 188. These irrigation and aspiration operations can remove cells which were killed by the heating process performed by expandable portion 182, which is similar to the heating process performed by expandable portion 114 of device 102 as discussed above.

Figure 12:
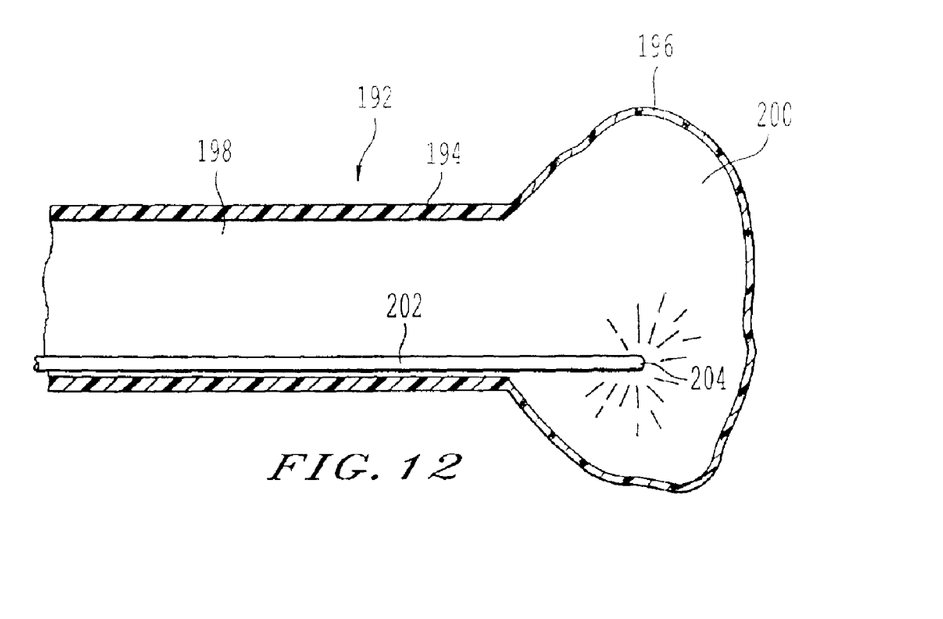
FIG. 12 is an cross-sectional view of a modification to the device shown in FIG. 2 which includes a probe.

As shown in FIG. 12, the device can be configured as device 192 which is similar to device 102. Device 192 includes a shaft portion 194 and an expandable portion 196, which are similar in construction to shaft portion 112 and expandable portion 114 of device 102. That is, shaft 194 defines a chamber 198 therein, and expandable portion 196 defines a chamber 200 therein. Heated fluid can be applied to chamber 200 via chamber 198 to expand expandable portion 196 in a manner similar to that described above with regard to device 102.

However, device 192 can further include a probe 202 that is inserted into chambers 198 and 200 as shown. The probe can be a metal heating probe, a fiber optic probe or any other suitable probe for delivering energy to the fluid in chamber 200. Specifically, as shown in FIG. 12, the probe 202 has a tip 204 from which energy such as thermoenergy, radiation, ultrasonic waves, microwaves, ultraviolet light waves, infrared light waves, or any other suitable energy can be emitted. Accordingly, the energy emitted from the tip 204 of probe 202 can heat the fluid contained in chamber 200, to thus thermally treat the cells at the site of interest in a manner similar to that described above with regard to device 102.

In addition, as mentioned above, a photosensitive material can be added to the fluid provided to chamber 200 to chemically treat the cells at the site of interest. The photosensitizers preferably are indocyanine green, but can be, for example, aminolevulinic acid, porphyrin derivatives, purine derivatives, NPE6, ATX-10, plant-derived photosensitizers, or other synthetic sensitizers such as $SNET_2$, Lutex, and the like. The concentration of the photosensitizers in the fluid should be at non-toxic levels.

Similar to expandable portion 114 discussed above, expandable portion 196 can be porous or can include openings therein to allow the fluid contained in chamber 200 to pass there through and contact or be absorbed by the cells at the site of interest. Accordingly, the photosensitizers contained in the fluid in chamber 200 can pass through the porous walls of expandable portion 196, or through openings in expandable portion 196, to come in contact with the cells at the site of interest, and be absorbed by the cells.

Assuming that the probe 202 is a fiber optic, light having a wavelength that will activate the photosensitizers contained in the fluid can be propagated through probe 202 and be admitted at the tip 204 of the probe. This light can be laser light, light generated by a LED, white light, or any other light of a wavelength that will activate the photosensitizers in the fluid. The activated photosensitizers that are in contact with or have been absorbed by the cells at the site of interest can alternate physically characteristic of those cells or, in other words, cause damage to those cells. Accordingly, in the example described above with regard to FIG. 1, the epithelial cells of the lens capsule 110 (see FIG. 1) can be damaged by the activated photosensitizers. This damage caused by the activated photosensitizers can kill the cells which have not been killed by the heating process, or can further damage the cells that have been damaged by the heating process to impede cell growth.

Figure 13:
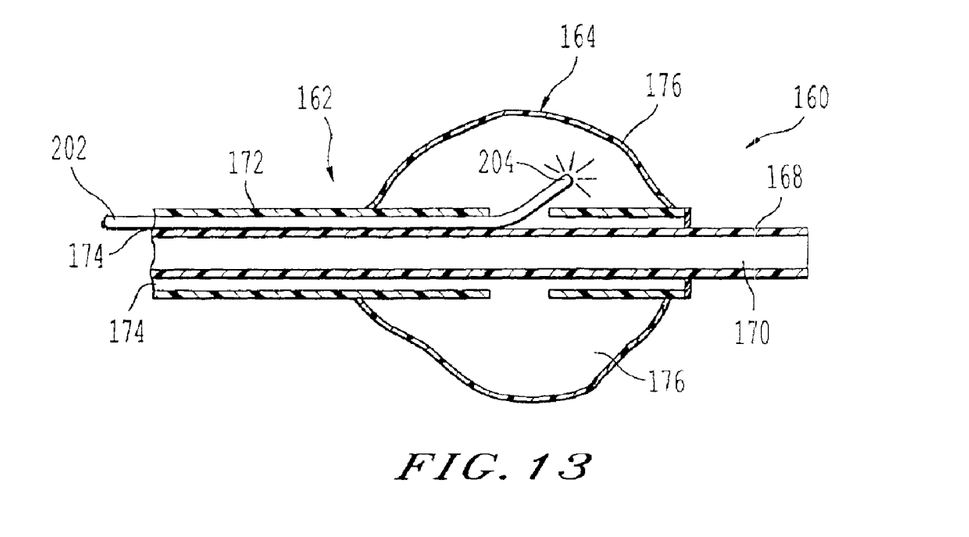
FIG. 13 is an example of a modification to the device as shown in FIG. 11 which includes a probe.

It is also noted that all the different configurations of the device as shown in FIGS. 4–11 can similarly include a probe 202 for purposes described above. For example, as shown in FIG. 13, the device 160 can include probe 202 in chamber 174 so that the tip 204 of the probe 202 extends into the chamber 1176 of the expandable portion 164. The probe 202 can be used as described above to heat the fluid, energize photosensitive materials contained of the fluid, or both.

It is also noted that the devices shown in FIGS. 2 and 4–13 as described above can be used to treat cells at locations in the body other than the lens capsule. For example, in the devices can be used to treat cells in blood vessels, skin and mucus tissues, the intestine, vagina, uterus, bladder, urethra, prostate, rectum, sinuses, brain, breast, heart, or any site in the body. The manner in which the devices are used to treat cells at these various locations in the body is similar to that described above with regard to the treatment of cells at the lens capsule.

That is, the device, such as device 102, is positioned so that the expandable portion 114 is in contact with or proximate to the cells to be treated. The heated fluid is then provided into the chamber 122 of expandable portion 114 in a manner described above to thermally treat the cells, and thus kill the cells without causing protein denaturation. The expandable portion 114 can be porous or can include openings as described above from which the fluid inside the chamber 122 can pass. As further described above, the fluid can include a photosensitizer which can come in contact with or be absorbed by the cells when the fluid passes through the pores or openings in the expandable portion 114. A probe 202 as shown, for example in FIG. 12, can be used to emits light of an appropriate wavelength to the cells of interest so that the photosensitizers in contact with or absorbed by the cells of interest are activated by the light, and thus change a physical characteristic of the cells or damage the cells as described above.

It is further noted that multiple devices can be used to perform the heating and photosensitizing process period. That is, a device such as device 102 can include an expandable portion 114 that is not porous or has no openings therein, and can be used in a manner similar to that described above to heat the cells at the site of interest to kill the cells without causing protein denaturation. That device can then be removed, and a second device having an expandable portion 114 that is permeable or has openings therein can be used to deliver the photosensitizer to the cells at the site of interest. This second device 102 can further include a probe 202 as described above which can be controlled to emit light which will activate the photosensitizers and thus cause the photosensitizer which have been absorbed by the cells or in contact with the cells to change the physical characteristic of the cells. The probe 202 could also be used to heat the fluid in the expandable portion 114 in the manner described above.

It is further noted that the devices as shown in FIGS. 2 and 4–13 as described above can be used to deliver other chemicals, such as antiproliferative drugs or anticancer chemicals, to the cells of the site of interest through openings or pores in their expandable portions. Furthermore, it is noted that the heating of the site of interest also expands the capillaries and vasculature at the site of interest, thus allowing more blood to flow to the site of interest. Accordingly, the photosensitizers or other drugs such as antiproliferative or anticancer chemical can be delivered systemically or, in other words, intravenously to the body. Because the drugs or chemicals are flowing through the body's blood stream, the drugs or chemicals will reach the site of interest through the expanded capillaries and vasculature. If the drugs or chemicals are photosensitizers, the device 102 or any of the other devices shown in FIGS. 4–13 can still be used to activate the photosensitizers at the site of interest.

That is, any of those devices can include a fiber optic probe 202 which can be used to emit light having a wavelength that activates the photosensitizers at the site of interest. The activated photosensitizers will then alter a physical characteristic of the cells at the site of interest as described above. It is noted that photosensitizers such as benzoporphynines can be activated with light having a wavelength between about 680 nm to about 695 nm, while NPE6 is activated by light having a wavelength between about 660 nm and about 670 nm. Lutex, on the other hand, is activated with light having a wavelength of about 725 nm, and $SNET_2$ is activated with light having a wavelength of about 660 nm to about 670 nm. It is further noted that the photosensitizers as well as the antiproliferative or anticancer chemicals can be delivered systemically to the site of interest or applied directly to the site of interest via any of the devices shown in FIGS. 2 and 4–13 as described above before, during, or immediately after the cells have been thermally treated to enhance the killing effect on the cells.

Figure 14:
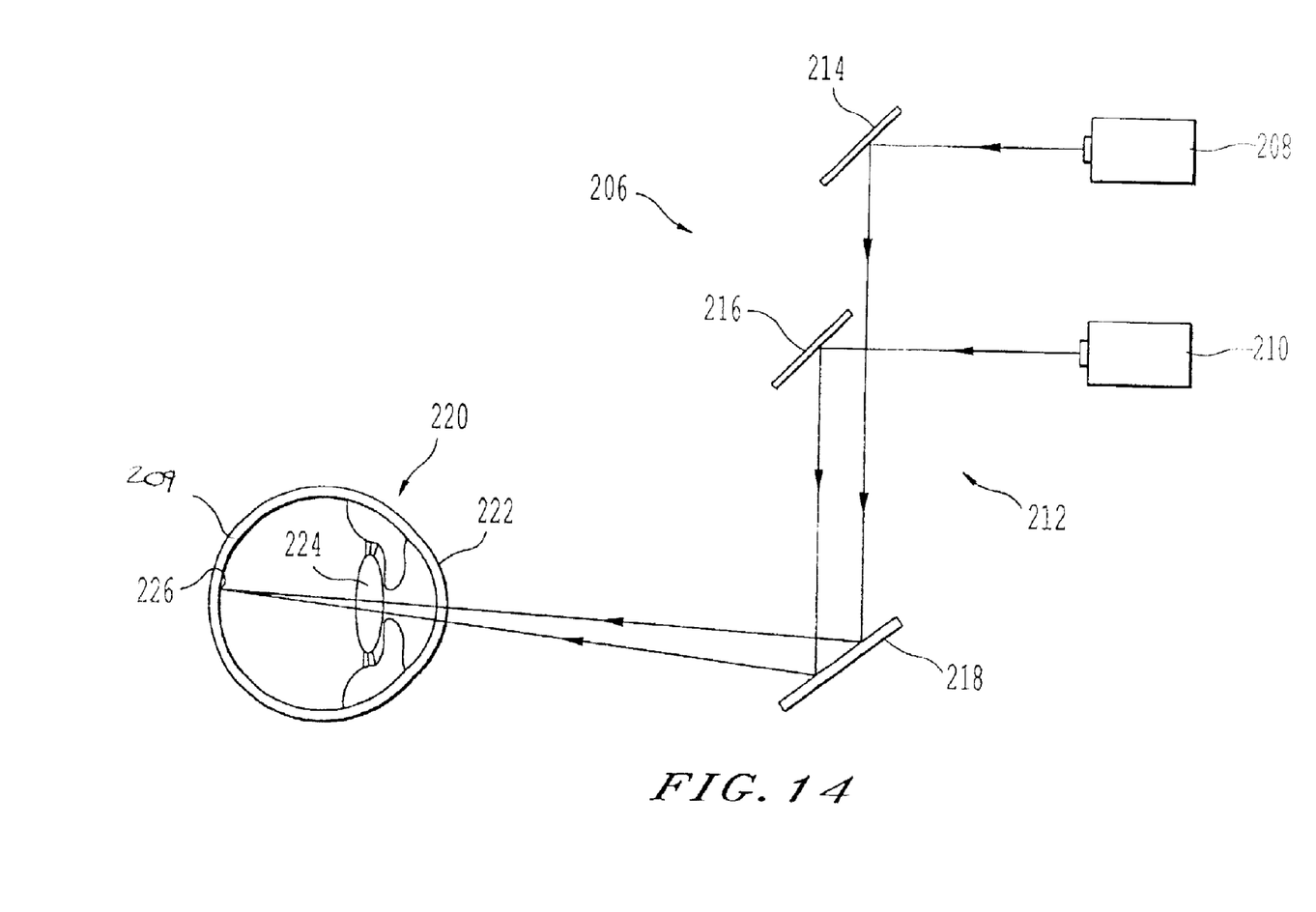
FIG. 14 is an example of a system for directing light from different sources onto the retina of the eye to treat cells on, in or under the retina of the eye according to an embodiment of the present invention.

Although FIGS. 1–13 and the above disclosure describe a device having an expandable portion for treating cells at the site of interest, other types of devices can be used to provide the same or similar treatment. For example, as shown in FIG. 14, a system 206 can include a plurality of light emitting devices 208 and 210 which can be, for example, lasers, LED's or any other type of light-emitting devices known in the art. Light-emitting device 208 emits light to a mirror arrangement 212, for example, which includes mirrors 214, 216 and 218. Accordingly, light being emitted by light-emitting device 208 is reflected by mirrors 214 and 218, and can be directed toward an eye 220 such that the lightwaves pass through the cornea 222 and are focused by the lens 224 onto a desired site on the retina 226. Similarly, the light being emitted by light emitting device 210 is reflected by mirror 216 and mirror 218 to enter the eye 220 and be focused by lens 224 on the desired site on retina 226.

In the system shown in FIG. 14, one of the light-emitting devices, for example, light-emitting device 208, can emit light such as laser light, infrared light, ultraviolet light, or any other suitable type of light, having a wavelength and intensity which will feed the cells on, in or under the portion of the retina 226 onto which the light propagates. The light-emitting device 208 can be controlled so that the intensity of the light will only heat the cells to a temperature below, for example, 60° C., to cause cell death without causing protein denaturation and thus, coagulation of the cells. Preferably, the cells are heated to a temperature within the range of about 42° C. to about 50° C. The cells also are exposed to the light for an appropriate amount of time, such as 1 to 10 minutes, as necessary, to effectively kill the cells without overheating the cells to cause protein denaturation to occur. It is further noted that the light-emitting device 208 could alternatively be a microwave emitting device, ultrasonic emitting device, radiation emitting device, or any other suitable energy emitting device as described above which will sufficiently heat the cells to thermally treat the cells as described above.

Before, during or after the light-emitting device 208 is controlled to heat the cells in the manner described above, a photosensitizer of the type as described above can be delivered to the site of interest at the retina 226 either locally through the use of a device such as that shown in FIGS. 2 and 4–13, or systemically through the patient's blood stream as described above. Once the cells have been thermally treated by the light being emitted from light-emitting device 208, light-emitting device 210 can be controlled to emit light having a wavelength which will activate the photosensitizer that have been absorbed by or are in contact with the cells at the site of interest on the retina 226. In one example, the light emitted by light-emitting device 208 to heat the cells can have a wavelength between about 700 nm to about 1200 nm. However, the light emitted by the light-emitting 210 nm. should have a wavelength which activate the photosensitizer used. For example, if NPE6 is used, the wavelength of the light should be about 664 nm.

Figure 15:
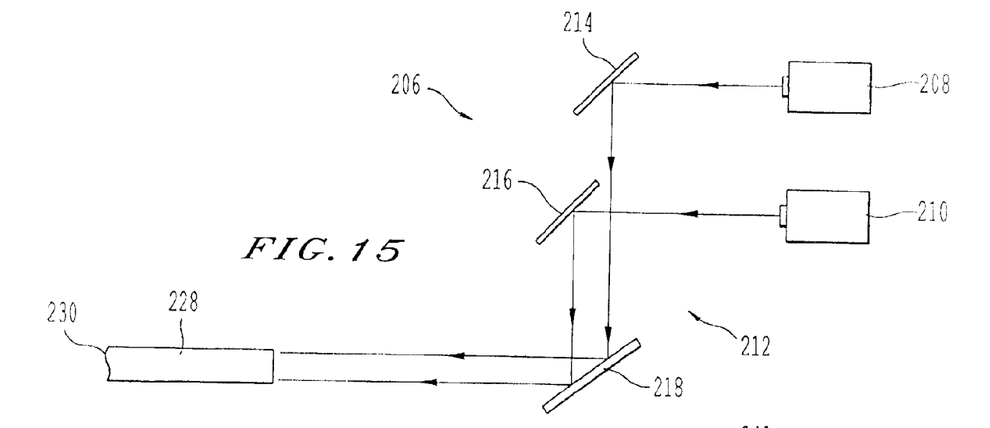
FIG. 15 is an example of a system as shown in FIG. 14 which is modified to include a fiber optic device into which the light from the different light sources is directed.

It should be also understood that the light being emitted by light-emitting device 210 can be emitted before, during or after the heat-treating process. It is further noted that the heat-treating process could be performed using a device as shown, for example, in FIGS. 2 and 4–13, while the photosensitizers can be activated using a light-emitting device, such as light-emitting device 210 as described above. It is further noted that the system 206 described above for delivering different types of light to a site of interest in a body can be modified in several ways. For example, as shown in FIG. 15, the system 206 can be configured to include a fiber optic device 228, which can be a flexible fiber optic cable or probe, or any other suitable type of fiber optic device that can receive the light being emitted by light-emitting devices 208 and 210. The distal end 230 of the fiber optic device 228 can then be aimed to the site of interest in a body, for example, at a site of interest on the retina 226 (see FIG. 14), or at any other site of interest in the body. The fiber optic probe 228 can also be inserted into the body so that the tip 230 can be placed proximate to the site of interest.

Figure 16:
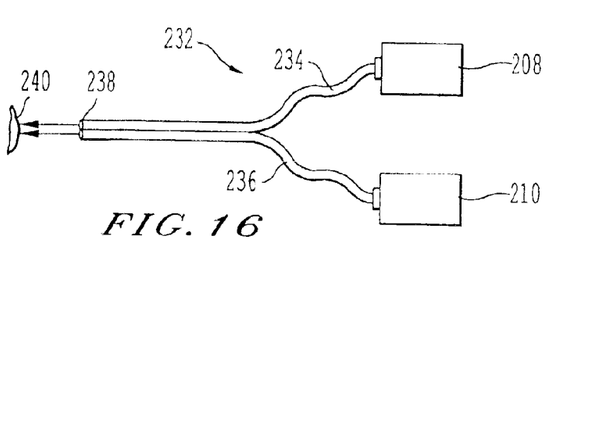
FIG. 16 is an example of a system shown in FIG. 14 which is modified to include fiber optic cables for propagating the light from the different light sources.
Figure 17:
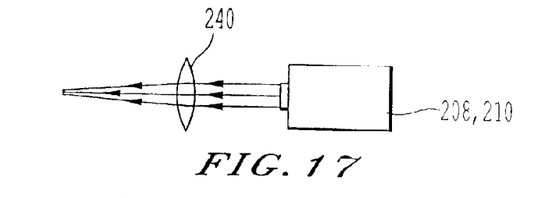
FIG. 17 is an example of a light source as included in the system shown in FIG. 14, having a converging lens for converting the light being emitted from the light source.
Figure 18:
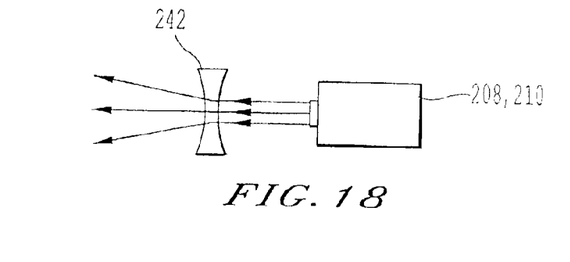
FIG. 18 is an example of a light source as included in the system shown in FIG. 14, having a diverging lens for converting the light being emitted from the light source.

As further shown in FIG. 16, the light-emitting devices 208 and 210 can instead be attached to a fiber optic probe 232 having a first fiber optic cable 234 and a second fiber optic cable 236. The tip 238 of the fiber optic probe can be aimed toward or placed proximate to a site of interest 240 in a body, such as at a site of interest on the retina 226 (see FIG. 14) or at any other site in a body, so that the light emitted by light-emitting devices 208 and 210 can radiate onto the site of interest to treat the cells in a manner described. As shown in FIG. 17, a converging lens 240 can be used in conjunction with either light-emitting sources 208 or 210 to converge the light being emitted by either of those light sources to a point, so that the light can be focused more precisely on a site of interest, or be received more efficiently into a fiber optic probe, such as fiber optic probe 228 in FIG. 15. Also, as shown in FIG. 18, a diverging lens 242 can be used with either of the light-emitting devices 208 or 210 to diverge the light rays being emitted by those light-emitting devices so that the light waves can cover a larger area of the site of interest.

Figure 19:
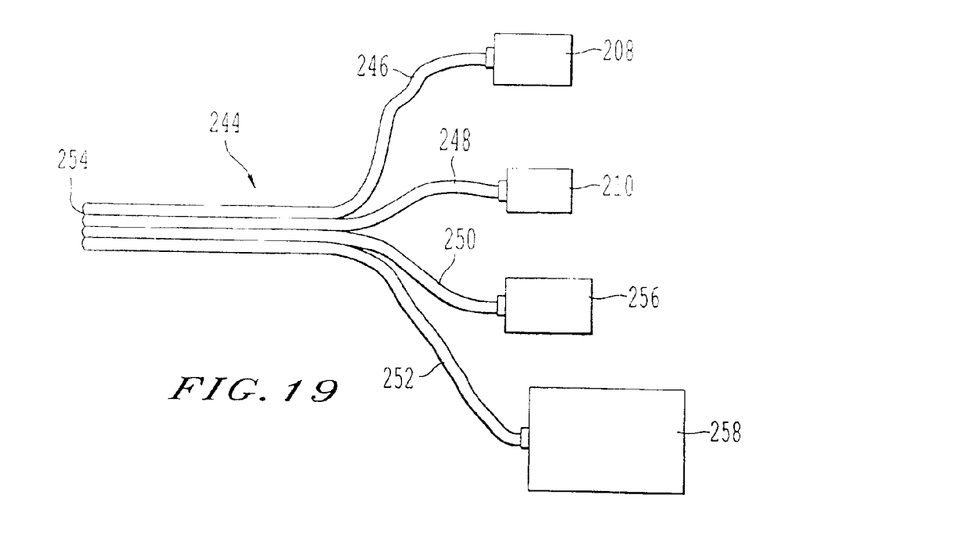
FIG. 19 is an example of a modification to the system shown in FIG. 16.

In addition, as shown in FIG. 19, light-emitting devices 208 and 210 can be coupled to a fiber optic device 244 having fiber optic cables 246, 248 250 and 252. In this example, light-emitting device 208 is coupled to fiber optic cable 246, and light-emitting 210 is coupled to fiber optic cable 248. Accordingly, the light being emitted by light-emitting devices 208 and 210 is emitted from the tip 254 of the fiber optic probe 244 to propagate onto the site of interest to treat the cells at the site of interest in the manner described above.

Furthermore, fiber optic cable 250 can be coupled to an illumination source 256 which can provide light which passes out of the tip 254 of fiber optic probe 244 to illuminate the site of interest. Furthermore, fiber optic cable 252 can be coupled to a monitor 258, such a television monitor, fluoroscope, CT-scan, or any other similar device, which can be used to monitor the site of interest that is being illuminated by the light emitted from illumination device 256 and is being treated by the light emitted by light-emitting devices 208 and 210.

Figure 20:
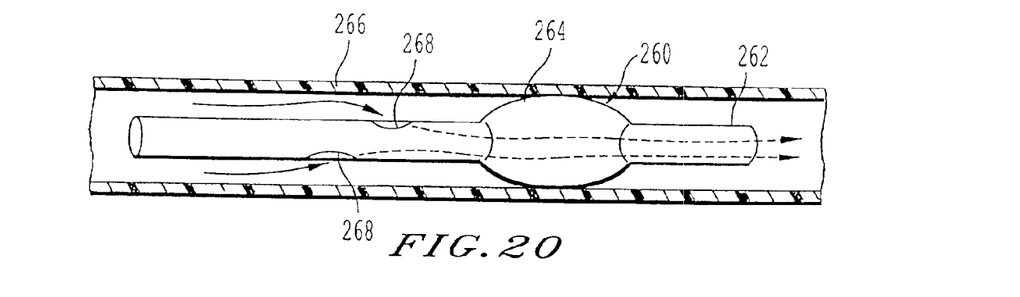
FIG. 20 is an example of a device for treating cells according to another embodiment of the present invention.
Figure 21:
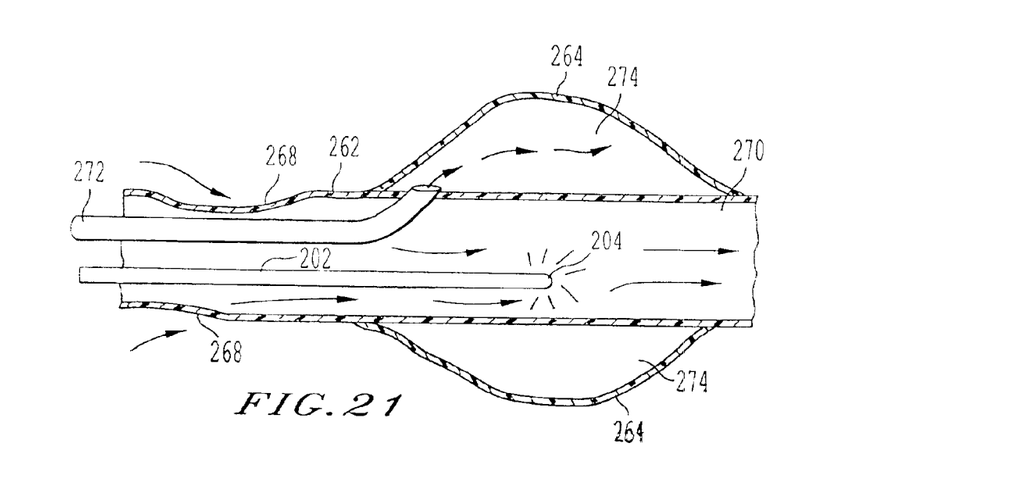
FIG. 21 is a cross-sectional view of the device shown in FIG. 20.

It is further noted that the devices described above with regard to FIGS. 2 and 4–13 can be modified in other ways to better suit the application in which they are being used. For example, as shown in FIGS. 20 and 21, a device 260 having a shaft portion 262 and expandable portion 264 similar to shaft portion 112 and expandable portion 114 described above can be used to treat cells at a site of interest within, for example, a patient's vasculature 266. In order to allow blood to flow more freely through the device 260, the shaft 262 can be configured with openings 268 therein, which will allow blood to freely flow through the chamber 270 defined by shaft portion 262.

As shown in FIG. 21 specifically, a tube 272 can be in communication with the chamber 274 of expandable portion 264 to provide a heated fluid to the chamber 274 to thus expand the chamber 264 and heat the cells at the site of interest in a manner similar to that described above with regard to, for example, device 102. It is note that the chamber 270 does not communicate with chamber 274 in this example. Furthermore, the device 260 can also include a probe 202 similar to that described above which can emit energy, such as light energy, microwave energy, ultrasonic energy, or any other suitable energy at its tip 204 to activate photosensitizers that have been delivered to the cells at the site of interest by the fluid leaking through the pores or openings in expandable portion 264, or systemically through the patient's blood stream. The energy can also be used to heat the fluid in the chamber 274.

Furthermore, indocyanine green (ICG) can be placed in the eye to alter cells therein. ICG is an agent that is known in the art and has been used in ophthalmology and cardiology for angiography of the back of the eye and for cardiac function, respectively. Specifically, ICG has been used on to enhance coagulation of portions of the eye. ICG absorbs a wavelength of between about 800 nm and about 810 nm and has a fluorescence of between about 820 nm and about 830 nm. To activate ICG, a fluorescent light passes through a filter and activates the fluid in which the ICG has been dissolved or applied. The image is then captured by an image intensifier for ICG angiography. For a further discussion of ICG, see U.S. Pat. No. 2,895,955, which is incorporated herein by reference.

However, using the above described methods, ICG can be used in conjunction with Transpupillary Thermotherpy (TTT or hyperthermia). At an increased concentration, ICG lowers the threshold for the damage to the choroid 209 (see FIG. 14). It has been determined that ICG creates a difference in the threshold at which damage occurs in choroidal vessels and retinal vessels during TTT treatment. The choroidal vessels can be closed or altered quicker or at lower power levels than the retinal vessels and therefore, treatment of choroidal neovascularization in age related macular degeneration is possible, while simultaneously protecting the retinal vessels. For examples of the threshold power levels for the choroidal vessels for pigmented and non-pigmented rabbits, and the change in the threshold power levels for the choroidal vessels with the addition of ICG, are shown in the following charts:

Transpupillary Thermotherapy
TTT Thresholds for Pigmented Rabbits

| Spot size | Power (mW)/60 sec. |
| --- | --- |
| 2 mm | 120–150 |
| 2 mm with compression | 80–100 |
| 3 mm | 200 |
| 3 mm with compression | 140 |

TTT Thresholds for Non Pigmented Rabbits

| Spot size | Power (mW)/60 sec. |
| --- | --- |
| 2 mm | 1500 |
| 2 mm with compression | 1400 |
| 2 mm with ICG, 0.4 mg/kg | 1250 |
| 2 mm with ICG, 0.8 mg/kg | 1250 |
| 2 mm with ICG, 1.4 mg/kg | 750 |
| 2 mm with ICG, 0.8 and 1.4 mg/kg on the retinal vessels | 2000 the vessels were patent (meaning open) |
| 3 mm | 1800 |
| 3 mm with compression | 1800 |
| 3 mm with ICG, 0.4 mg/kg | 1250 |
| 3 mm with ICG, 0.8 mg/kg | 1000 |
| 3 mm with ICG, 1.4 mg/kg | 750 |
| 3 mm with ICG, 0.8 and 1.4 mg/kg on the Retinal vessels | 2000 the vessels were patent (meaning open) |

As shown specifically in the above chart, as the concentration of ICG is increased from 0 to 1.4 mg/kg of body weight of the subject, the power required to damage the choroidal vessels decreases from 1500 mW to 750 mW, while the power to alter or close the retinal vessels remains substantial the same for the varying concentrations of the ICG. However, as noted above the subjects in the chart are pigmented and non-pigmented rabbits. The amount of power required to damage the choroidal vessels in a human patient varies according to the pigmentation, the time the power is applied and size (diameter) of the spot. For example, the power to damage the choroidal vessels in a human for a non pigmented spot of about 3 nm in diameter is about 1500 mW or less for 60 seconds. It would be necessary to alter the time and/or power of the application of the light emitting device depending on the particular size and pigmentation of the spot.

ICG is preferably injected intravenously in the amount of between about 1 mg/kg to about 15 mg/kg of a patient's body weight, and more preferably, in the amount of about 1 mg/kg to about 3 mg/kg. In another embodiment, a fluid containing ICG is introduced to the patient in an amount to provide about 0.4 mg/kg to about 1.4 mg/kg based on the patient's body weight. As seen in FIG. 14, a laser diode 208 and/or 210, or any other light emitting device, is then aimed and energized at a predetermined level of power, preferably between about 1500 mW or less to activate the ICG and the desired area of the eye. However, the light emitting device can be energized at any desired power that would achieve the desired result. Since ICG is a fluorescent dye, it can be used for simultaneously seeing and treating the cells. The ICG will then alter a physical characteristic of the cells at the site of interest, as described above, to kill or impede multiplication of the choroid cells. Preferably, the ICG will alter the choroidal cells, like a photsensitzer, thus treating the choroidal neovascularization while not altering the retinal cells.

Additionally, ICG can be used to damage the lens epithelium, by injecting ICG into the lens capsule and using laser light of about 800 nm to about 810 nm. As seen in FIG. 1, preferably, device 102 is used to apply a fluid or material containing ICG. The device is inserted into the eye and applies the fluid or material to the lens capsule 110 of eye 100, similar to the application of the material described above. The concentration of ICG is preferably about 1–200 micograms per milliliter of fluid, with the fluid preferably being saline solution. However, the fluid may be any type of fluid that would not adversely affect the eye, when applied to the eye, and the concentration of ICG can be any concentration that would achieve the desired results. Once the material or fluid is applied, the ICG can be activated using a diode laser or any other light emitting device that is preferably directed to the ICG by optical fiber, as described above. The light emitting device can either be attached to device 102 or can be separate. Additionally, if desired, the light emitting device can activate the ICG from a position that is outside of the eye 100, as described above. The fluid having a concentration of ICG may be used in any of the above described application devices and is not limited to device 102.

The ICG not only absorbs the light from the light emitting device, but also has some photosensitizing capabilities, which can thus damage the lens cell membrane when exposed to light having the above described wavelengths. This damage, however, is different than photocoagulation where protein denaturation occurs. By using ICG, most of the damage to the cell membrane occurs above the body temperature and below the temperature of 60 degrees Celsius, which is the temperature at which protein denaturization typically occurs. Heating the cells at this temperature range thus minimizes the coagulative effect on the surrounding tissues.

It is also noted that the cells can be irradiated with radiation before, during or after being treated thermally in the manners described above. The radiation can be delivered by the same device, such as device 102, that is used to heat the cells to perform the hyperthermia treatment as described above. Specifically, the shaft portion of the device can be covered with or otherwise include a protective shield that prevents radiation from escaping the device. The expandable portion allows radiation to be emitted therefrom, although a portion of the expandable portion of the device can also include a protective shield.

The radiation used to treat the cells can be either beta radiation with a very short span, such as radiation emitted by strontium or iridium. However, gamma radiation such as that emitted by $P^{32}$, Iodine 95, Palladium 90, or so on, can also be used. The other isotopes used in the solution can be tritiated (radioactive hydrogen), radioactive carbon, and so on. The components described above which emit the radiation can be made into small particles which are included in the fluid that is delivered into the expandable portion of the device as described above. Accordingly, the fluid will heat the cells of interest to kill the cells or impede cell growth, and the radiation will further enhance the cell killing effect.

The hyperthermia technique of heating the cells can also be performed prior to irradiating the cells with radiation. In this event, separate devices can be used to heat the cells and irradiate the cells. It is also noted that the photosensitizer techniques described above can also be performed. Furthermore, antiproliferative drugs or anticancer drugs can also be applied to the cells at the site of interest.

It is also noted that this technique of using the device to treat cells with radiation as described above can be used to treat cells at any suitable site in the body. More particularly, it can be noted that when treating cells of the lens capsule, such as epithelial cells as described above, it is not necessary to heat the cells if the radiation technique is used. Rather, radiation alone can be applied to the cells of the lens capsule by the device, such as those described above, to kill the cells or impede cell growth. However, it can be also be advantageous to treat the cells of the lens capsule with heat and radiation, a well as with photosensitizers, antiproliferative and anticancer drugs.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

What is claimed is:

1. A system for treating cells of an eye in a patient, comprising:
   an energy emitting device having a container to receive and contain a fluid and adapted to emit energy to heat said cells to a temperature which is above body temperature and below a temperature at which protein denaturation occurs in said cells, to kill said cells or impede multiplication of said cells; and
   a material delivery device that delivers said fluid including indocyanine green to said cells, said fluid being adapted to alter a physical characteristic of said cells.

2. A system as claimed in claim 1, wherein:
   an amount of said indocyanine green in said fluid is between about 0.4 mg/kg to about 1.4 mg/kg of the patient's body weight.

3. A system as claimed in claim 1, wherein:
   said energy emitting device includes a laser diode.

4. A system as claimed in claim 1, wherein:
   said material delivery device delivers said fluid intravenously.

5. A system as claimed in claim 1, wherein:
   said energy emitting device includes a laser diode, which is adapted to emit said energy to activate said indocyanine green portion of said fluid.

6. A system as claimed in claim 1, wherein:
   a concentration of said indocyanine green is between about 1 microgram and 200 micrograms per milliliter of said fluid.

7. A system as claimed in claim 1, wherein:
   said fluid container is adapted to expand when receiving said fluid therein.

8. A system as claimed in claim 1, wherein:
   said fluid container comprises a permeable membrane, which is adapted to release at least some of said fluid contained in said fluid container.

9. A system as claimed in claim 1, wherein:
   said fluid container comprises a wall having at least one opening therein, which is adapted to release therethrough at least some of said fluid contained in said fluid container.

10. A system as claimed in claim 1, wherein:
said energy emitting device and said material delivery device are configured as a unitary device, which is adapted to emit said energy to heat said cells and to deliver said fluid to said cells.

11. A system as claimed in claim 10, wherein:
said unitary device comprises a fluid container, adapted to receive and contain a fluid therein which emits said energy as thermal energy; and
said fluid container is further adapted to release therefrom at least some of said fluid, to enable said material to contact said cells.

12. A system as claimed in claim 1, further comprises
a light emitting device, adapted to emit light energy which activates said indocyanine green in contact with said cells to cause said activated indocyanine green to kill or impede multiplication of said cells.

13. A method for treating choroidal cells in of an eye of a patient, comprising the steps of:
positioning an energy emitting device at a position in relation to said choroidal cells;
emitting energy from said energy emitting device and directing said energy to said choroidal cells to heat said choroidal cells to a temperature which is above body temperature and below a temperature at which protein denaturation occurs in said choroidal cells, to kill said choroidal cells or impede multiplication of said choroidal cells;
introducing a fluid to the choroidal cells of the eye, said fluid including indocyanine green; and
activating said indocyanine green that is in contact with said choroidal cells to cause said indocyanine green to kill or impede multiplication of said choroidal cells.

14. A method as claimed in claim 13, wherein:
a concentration of indocyanine green is between about 0.4 mg/kg to about 15 mg/kg of the patient's body weight.

15. A method as claimed in claim 13, wherein:
said activating step includes activating said indocyanine green with light emitted by a laser diode.

16. A method as claimed in claim 13, wherein
said introducing step includes introducing said fluid intravenously.

17. A method as claimed in claim 13, wherein:
said positioning step includes positioning a laser diode device at a position in relation to said choroidal cells.

18. A method for treating cells of an eye, comprising the steps of:
positioning an energy emitting device having a container containing a fluid including indocyanine green, at a position in relation to said cells; and
causing said energy emitting device to emit energy which activates the indocyanine green and heats said cells to a temperature which is above body temperature and below a temperature at which protein denaturation occurs in said cells, to kill said cells or impede multiplication of said cells.

19. A method as claimed in claim 18, wherein:
said container is expandable; and
said positioning step includes positioning said fluid in said container at a pressure sufficient to expand said container.

20. A method as claimed in claim 18, wherein:
said container comprises a permeable membrane; and
said positioning step includes positioning said fluid in said container such that at least some of said fluid contained in said container exits said container through said permeable membrane.

21. A method as claimed in claim 18, wherein:
said container comprises a wall having at least one opening therein; and
said positioning step includes positioning said fluid in said container such that at least some of said fluid contained in said container exits said container through said at least one opening.

22. A method as claimed in claim 18, wherein
the causing step includes causing a light emitting device, adapted to emit said energy as light energy which activates said indocyanine green in contact with said cells to cause said activated indocyanine green to kill or impede multiplication of said cells.

23. A method as claimed in claim 18, wherein
said positioning step includes positioning said energy emitting device in relation to choroidal cells of the eye.

24. A method of treating cells in the eye of a patient comprising the steps of:
heating cells in a target site in the eye to a temperature above body temperature and below a temperature at which protein denaturation occurs in said cells and for sufficient time to kill at least a portion of said cells in said target site or impede multiplication of said cells;
delivering a photosensitive material to said target site, said photosensitive material being capable of altering a physical characteristic of said cells; and
applying a light source to said target site and activating said photosensitive material to treat said cells in said target site.

25. The method of claim 24, comprising directing a first laser beam to said target site to heat said cells in said target site, and where said light is a second laser beam having a wavelength sufficient to activate said photosensitive material.

26. The method of claim 25, wherein said target site is on or in the retina.

27. The method of claim 26, comprising introducing said photosensitive material into the blood stream of the patient to flow to said retina, and thereafter activating said photosensitive material on or in the retina.

28. The method of claim 27, wherein said second laser beam to activate said photosensitive material is applied before, during or after heating the cells in the target site of the retina.

29. The method of claim 24, wherein said photosensitive material is selected from the group consisting of aminolevulinic acid, porphyrin derivatives, purine derivatives, NPE6, ATX-10, $SNET_2$ and Lutex.

30. A method of treating cells in the retina of the eye of a patient comprising the steps of:
directing a first laser light beam to a target site in the retina of said eye for a time sufficient to heat cells in said target site to a temperature above body temperature and below a protein denaturation temperature to kill or impede multiplication of at least a portion of cells in said target site;
introducing a photosensitive material into the blood stream of the patient to flow through the target site in the retina, said photosensitive material being capable of altering a physical characteristic of said cells; and applying a second laser light beam to said target site to activate said photosensitive material to treat said cells in said target site of said retina.

31. The method of claim 30, wherein said second laser beam to activate said photosensitive material is applied before, during or after heating the cells in the target site of the retina.

32. The method of claim 30, wherein said photosensitive material is selected from the group consisting of aminolevulinic acid, porphyrin derivatives, purine derivatives, NPE6, ATX-10, $SNET_2$ and Lutex.

33. A method of treating cells in the retina of a patient comprising the steps of:

positioning an energy emitting device at a position in relation to said cells in a target site of the retina; and directing energy from said energy emitting device to heat cells in the retina to a temperature above body temperature and below a protein denaturation temperature to kill or impede multiplication of at least a portion of cells in said target site on the retina.

34. The method of claim 33, further comprising the step of:

introducing a photosensitive material into the target site of the retina, and applying a light source to said target site to activate said photosensitive material to treat the cells in said target site with said photosensitive material.

35. The method of claim 33, wherein said energy emitting device is a laser and said method comprises directing a laser beam to said target site for a time sufficient to heat the cells in said target site.

36. The method of claim 34, wherein said light source is a laser beam having a wavelength sufficient to activate said photosensitive material.

37. The method of claim 33, comprising the step of introducing said photosensitive material into the blood stream of said patient to flow to said retina and said method comprising focusing said laser beam on the retina to activate said photosensitive material.

38. The method of claim 37, wherein said laser beam to activate said photosensitive material is applied before, during or after heating the cells in the target site of the retina.

39. The method of claim 37, wherein said photosensitive material is selected from the group consisting of aminolevulinic acid, porphyrin derivatives, purine derivatives, NPE6, ATX-10, $SNET_2$ and Lutex.

40. The method of claim 24, wherein said target site is the choroid.

41. The method of claim 24, wherein said target site is under the retina.

42. A method of treating cells on, in or under the retina of the eye of a patient comprising the steps of:

heating cells in a target site on, in or under the retina of the eye to a temperature above body temperature and below a temperature at which protein denaturation occurs in said cells and for sufficient time to kill at least a portion of said cells in said target site or impede multiplication of said cells;

delivering a photosensitive material into the bloodstream of the patient to flow to said retina and to said target site, said photosensitive material being capable of altering a physical characteristic of said cells; and applying a light source to said target site and activating said photosensitive material to treat said cells in said target site.

43. The method of claim 42, comprising directing a first laser beam to said target site to heat said cells in said target site, and where said light source is a second laser beam having a wavelength sufficient to activate said photosensitive material and treat said cells in said target site on, in or under the retina.

44. The method of claim 42, wherein said target site is under the retina.

45. The method of claim 42, wherein said second laser beam to activate said photosensitive material is applied before, during or after heating the cells in the target site of the retina.

46. The method of claim 42, wherein said photosensitive material is selected from the group consisting of aminolevulinic acid, porphyrin derivatives, purine derivatives, NPE6, ATX-10, $SNET_2$ and Lutex.

47. A method of treating cells in the eye of a patient comprising the steps of:

directing a first laser light beam to a target site in the choroid or under the retina of said eye for a time sufficient to heat cells in said target site to a temperature above body temperature and below a protein denaturation temperature to kill or impede multiplication of at least a portion of cells in said target site;

introducing a photosensitive material into the blood stream of the patient to flow through the target site in the choroid or under the retina, said photosensitive material being capable of altering a physical characteristic of said cells; and applying a second laser light beam to said target site to activate said photosensitive material to treat said cells in said target site in the choroid or under the retina.

48. The method of claim 47, wherein said second laser beam to activate said photosensitive material is applied before, during or after heating the cells in the target site of the retina.

49. The method of claim 47, wherein said target site is in the choroid of the eye.

50. The method of claim 47, wherein said target site is under the retina.

* * * * *